United States Patent [19]
Djuric et al.

[11] Patent Number: 5,990,326
[45] Date of Patent: Nov. 23, 1999

[54] 3-OXIRANYL BENZOIC ACIDS AND DERIVATIVES THEREOF

[75] Inventors: Stevan Wakefield Djuric, Glenview; Thomas Dale Penning, Des Plaines, both of Ill.

[73] Assignee: G.D. Searle & Co., Skokie, Ill.

[21] Appl. No.: 07/976,614

[22] Filed: Nov. 16, 1992

Related U.S. Application Data

[62] Division of application No. 07/274,218, Sep. 21, 1988, abandoned.

[51] Int. Cl.$^6$ .................................................. C07D 303/16
[52] U.S. Cl. ............................................. 549/561; 514/475
[58] Field of Search ............................. 549/561; 514/475

[56] References Cited

U.S. PATENT DOCUMENTS

| | | | |
|---|---|---|---|
| 4,665,189 | 5/1987 | Baker et al. | 549/554 |
| 4,675,335 | 6/1987 | Baker et al. | 514/381 |

FOREIGN PATENT DOCUMENTS

| | | |
|---|---|---|
| 0134111 | 7/1984 | European Pat. Off. . |
| 2144422 | 7/1984 | United Kingdom . |
| 2177401 | 7/1984 | United Kingdom . |

OTHER PUBLICATIONS

J. Evans, et. al., Prostaglandins, Leukotrienes and Medicine 23: 167–171 (1986).
R. A. Lewis, et. al., J. Clin. Invest., 73: 889–897 (1984).

*Primary Examiner*—Ba K. Trinh
*Attorney, Agent, or Firm*—Fitzpatrick, Cella, Harper & Scinto

[57] ABSTRACT

The present invention relates to compounds of the formula

III

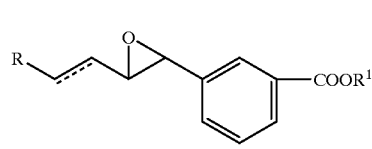

or a pharmaceutically acceptable salt thereof wherein R is alkyl of 12 carbon atoms, alkenyl of 12 carbon atoms having from 1 to 4 —CH═CH— groups when the carbon adjacent to R is saturated and from 1 to 2 —CH═CH— groups when the carbon adjacent to R is unsaturated, aryl, heterocyclo, alkoxyalkyl wherein the alkyl groups have 1 to 6 carbon atoms, or aryloxyalkyl wherein the alkyl group has 1 to 6 carbon atoms $R^1$ is hydrogen, lower alkyl, or a pharmaceutically acceptable cation. These compounds are inhibitors of leukotriene $A_4(LTA_4)$ hydrolase.

11 Claims, No Drawings

3-OXIRANYL BENZOIC ACIDS AND DERIVATIVES THEREOF

This is a division of application Ser. No. 07/274,218, filed Sep. 21, 1998, now abandoned.

BACKGROUND OF THE INVENTION (a) Field of the Invention

The present invention relates to 3-oxiranyl benzoic acids and derivatives thereof and their pharmaceutically acceptable salts. Compounds of the present invention are useful in treating inflammatory conditions in mammals such as psoriasis, Crohn's disease, ulcerative colitis, arthritis, gout and the like. Compounds of the present invention are inhibitors of epoxide hydrolases, specifically leukotriene $A_4$ ($LTA_4$) hydrolase which catalyzes the biochemical transformation of $LTA_4$ into leukotriene $B_4$ ($LTB_4$) which is a potent proinflammatory agent.

(b) Prior Art $LTB_4$ has been implicated as an important mediator of inflammation due to its potent proinflammatory properties. In neutrophils, $LTB_4$ production from the unstable allylic epoxide $LTA_4$ (Formula I) is catalyzed by a cytosolic enzyme $LTA_4$ hydrolase.

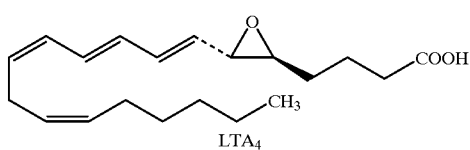

LTA4

$LTB_4$ (Formula II) is an arachidonic acid metabolite which is produced by the 5-lipoxygenase pathway. Pharmacologically, $LTB_4$ is an important mediator of inflammation in mammals. As a mediator of inflammation, $LTB_4$ is known to induce chemotaxis, chemokinesis, aggregation, and degranulation of leukocytes in vitro, and to induce accumulation of polymorphonuclear leukocytes, and increase vascular permeability and edema formation in vivo.

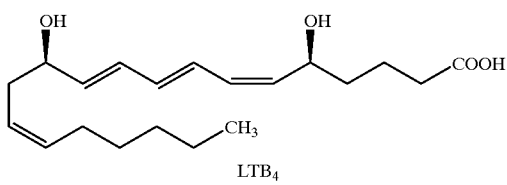

LTB4

Particularly high levels of $LTB_4$ are detected in lesions in inflammatory diseases such as rheumatoid or spondylarthritis, gout, psoriasis, ulcerative colitis, Crohn's disease, and some respiratory diseases.

Accordingly, it is an object of this invention to produce compounds for use as pharmaceutical agents which will inhibit $LTB_4$ activity in mammals by inhibiting $LTA_4$ hydrolase and preventing the formation of $LTB_4$.

U. K. Patent Applications GB 2177401 A and GB 2144422 A and their European counterpart EP-134111-A generically disclose compounds of the formula

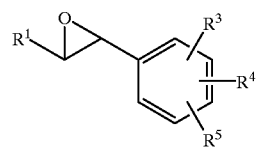

in which $R^1$ is an alkenyl or alkynyl group optionally substituted with an optionally substituted phenyl group and containing from 5 to 30 carbon atoms and, $R^3$, $R^4$, and $R^5$ are each selected from hydrogen, carboxyl $C_{2-5}$ alkoxycarbonyl, $C_{1-4}$ alkyl, $C_{1-4}$ alkoxy, hydroxyl, optionally protected tetrazolyl, halo, trifluoromethyl, nitrile, nitro, and $-CONR^{10}_2$ where each $R^{10}$ is hydrogen or $C_{1-4}$ alkyl. These compounds are intermediates useful for preparing pharmaceutical compounds of the formula

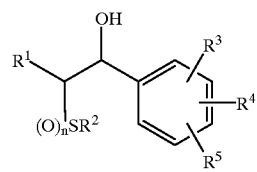

in which n is 0, 1 or 2, $R^1$ is hydrocarbyl group optionally substituted with optionally substituted phenyl group containing from 5 to 30 carbon atoms, $R^2$ is optionally substituted phenyl or $C_{1-10}$alkyl optionally substituted by one or more substituents selected from optionally protected hydroxyl, optionally protected carboxyl, nitrile, optionally protected tetrazolyl, $-COR^6$ where $R^6$ is $C_{1-4}$alkyl, $C_{1-4}$alkoxy, an optionally protected amino acid residue or $-NR_2^7$ where each $R^7$ is hydrogen or $C_{1-4}$alkyl, and $-NHR^8$ where $R^8$ is hydrogen, a protecting group, an optionally protected amino acid residue, $C_{1-4}$alkyl or $-COR^9$ where $R^9$ is $C_{1-4}$alkyl or $C_{1-4}$alkoxy, and $R^3$, $R^4$ and $R^5$ are each selected from hydrogen, carboxyl, $C_2$salkoxycarbonyl, $C_{1-4}$alkyl, $C_{1-4}$alkoxy, hydroxyl, optionally protected tetrazoyl, halo, trifluoromethyl, nitrile, nitro and $-CONR^{10}_2$ where each $R^{10}$ is hydrogen or $C_{1-4}$alkyl; and salts thereof. These compounds in unprotected form, are disclosed to be pharmacologically active in tests which demonstrate their antagonist effect on leukotriene receptors and indicate their use in the treatment of allergic disorders.

J. Evans, et al., PROSTAGLANDINS, LEUKOTRIENES AND MEDICINE, 23: 167–171 (1986) discloses compounds which inhibit rat and human neutrophil $LTA_4$ hydrolases; however, these compounds are structurally different from compounds of the present invention.

The pharmacology of the biologically active leukotrienes is generally discussed in J. CLIN. INVEST. 73: 889–897 (1984).

SUMMARY OF THE INVENTION

The present invention relates to compounds of the formula

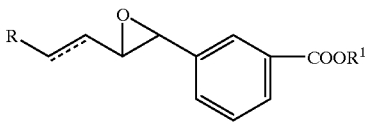

III or a pharmaceutically acceptable salt thereof wherein R is alkyl of 12 carbon atoms, alkenyl of 12 carbon atoms having from 1 to 4 —CH=CH— groups when the carbon adjacent to R is saturated and from 1 to 2 —CH=CH— groups when the carbon adjacent to R is unsaturated, aryl, heterocyclo, alkoxyalkyl wherein the alkyl groups have 1 to 6 carbon atoms, or aryloxyalkyl wherein the alkyl group has 1 to 6 carbon atoms; and $R^1$ is hydrogen, lower alkyl, or a pharmaceutically acceptable cation.

DETAILED DESCRIPTION OF THE INVENTION

This invention encompasses compounds of Formula III as previously described. A preferred embodiment of the present invention encompasses compounds of the formula

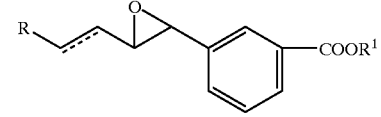

wherein R is alkyl of 12 carbon atoms, or alkenyl of 12 carbon atoms having from 1 to 3 —CH=CH— groups when the carbon adjacent to R is saturated and from 1 to 2 —CH=CH— groups when the carbon adjacent to R is unsaturated; $R^1$ is hydrogen or alkyl of from 1 to 4 carbon atoms; or a pharmaceutically acceptable salt thereof.

Included in the present invention are compounds of the formula

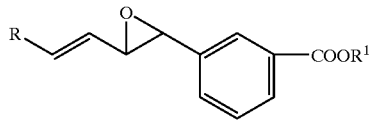

wherein R is alkyl of 12 carbon atoms or alkenyl of 12 carbon-atoms having from 1 to 2 —CH=CH— groups; $R^1$ is hydrogen or alkyl of from 1 to 4 carbon atoms; or a pharmaceutically acceptable salt thereof.

The present invention also includes compounds of the formula

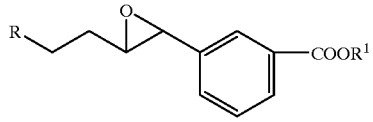

wherein R is alkenyl of 12 carbons having from 1 to 3 —CH=CH— groups; $R^1$ is hydrogen or alkyl of from 1 to 4 carbon atoms; and the pharmaceutically acceptable salts thereof.

The compounds encompassed by the present invention are not limited to any particular stereochemical configuration. Both cis and trans isomers are within the scope of the invention.

The present invention includes pharmaceutical compositions for the treatment of inflammatory conditions in mammals such as psoriasis, Crohn's disease, ulcerative colitis, arthritis, gout, and the like comprising a pharmaceutically acceptable carrier and a leukotriene $A_4$ ($LTA_4$) hydrolase inhibitor of the formula

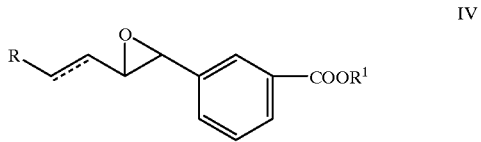

IV wherein R is alkyl of 12 to 16 carbon atoms, alkenyl of 12 to 16 carbon atoms having from 1 to 4 —CH=CH— groups, aryl, heterocyclo, alkoxyalkyl wherein the alkyl groups have 1 to 6 carbon atoms, or aryloxyalkyl wherein the alkyl group has 1 ato 6 carbon atoms; R' is hydrogen or lower alkyl; or a pharmaceutically acceptable salt thereof.

The term "lower alkyl" as used to describe $R_1$ means straight or branched chain alkyls having 1–6 carbon atoms.

The term "aryl" as used to describe R means phenyl or substituted phenyl.

The term "heterocycle" as used to describe R means pyridyl, thienyl, furan, and the like.

The term "pharmaceutically acceptable cations" as used to describe $R^1$ refers to cations such as ammonium, sodium, potassium, lithium, calcium, magnesium, ferrous, zinc, copper, manganous, aluminum, ferric, manganic, tetraalkylammonium, and the like.

The term "pharmaceutically acceptable salts" refers to those base derived salts of any compound herein having a carboxylic acid function.

The base derived salts can be derived from pharmaceutically acceptable non-toxic inorganic or organic bases. Among the inorganic bases employed to produce said pharmaceutically acceptable salts are the hydroxide bases of the "pharmaceutically acceptable cations" disclosed above.

Among the organic bases employed to produce said pharmaceutically acceptable salts are the pharmaceutically acceptable non-toxic bases of primary, secondary, and tertiary amines. Especially preferred non-toxic bases are isopropylamine, diethylamine, ethanolamine, dicyclohexylamine, choline, and caffeine. All the pharmaceutically acceptable non-toxic addition salts are prepared by conventional processes well known to those of ordinary skill in the art.

The present invention encompasses pharmaceutical compositions containing an effective therapeutic amount of a compound of Formula III along with a pharmaceutically acceptable carrier.

The invention also includes a method of treating inflammatory conditions in animals by administering an anti-inflammatory effective amount of a compound of Formula III or Formula IV.

The compounds described herein may be prepared by any available procedure. The compounds of this invention are generally prepared according to the reaction schemes set out in Schemes A to F.

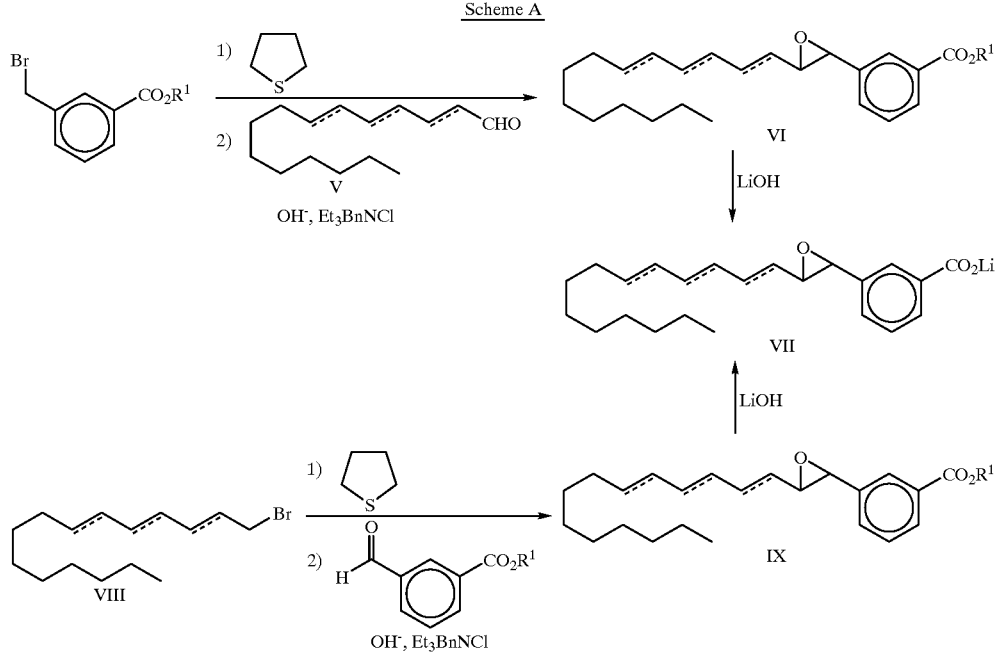
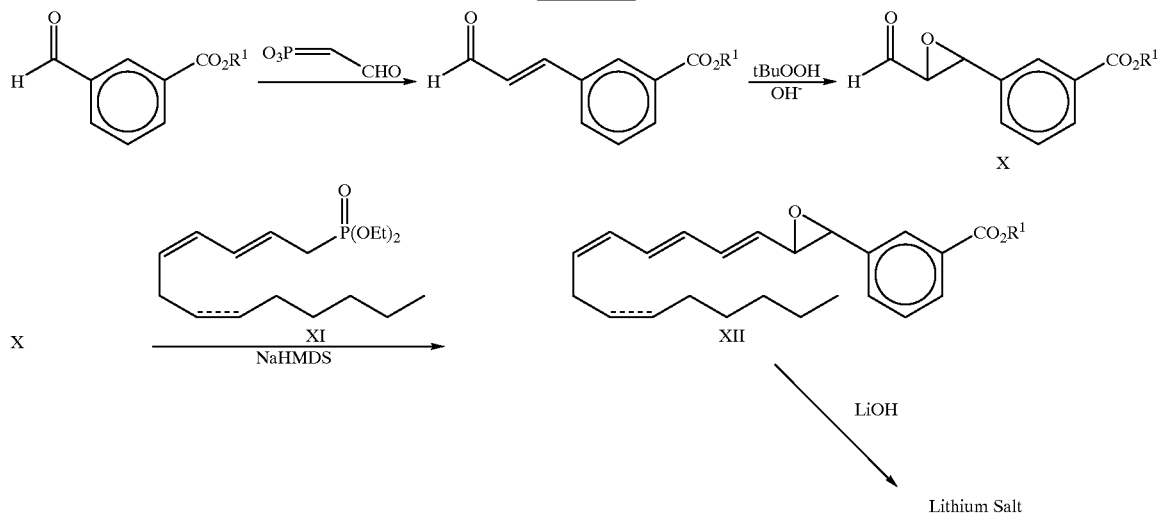

SCHEME C

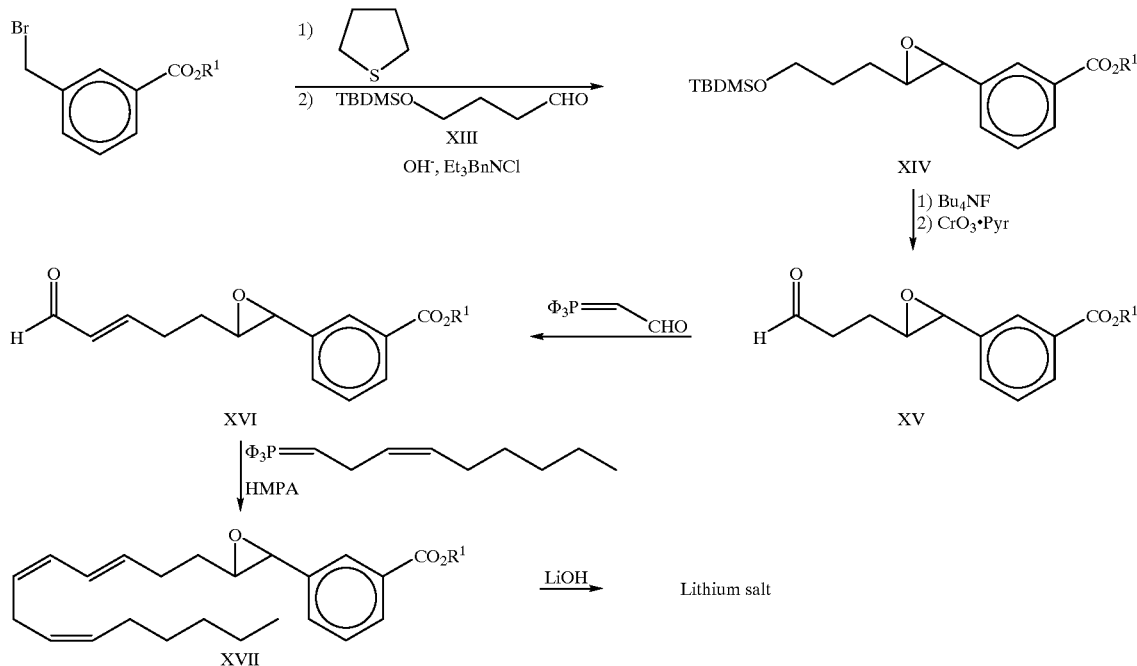

SCHEME D

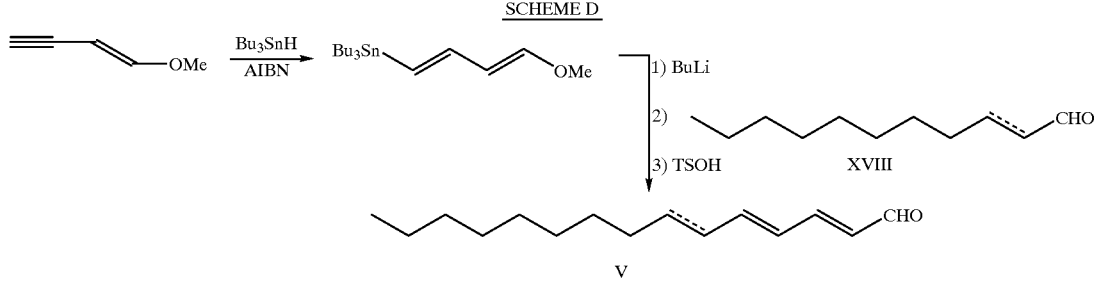

SCHEME F

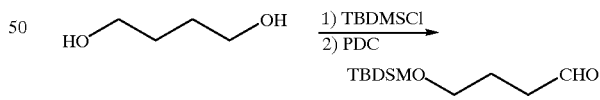

SCHEME E

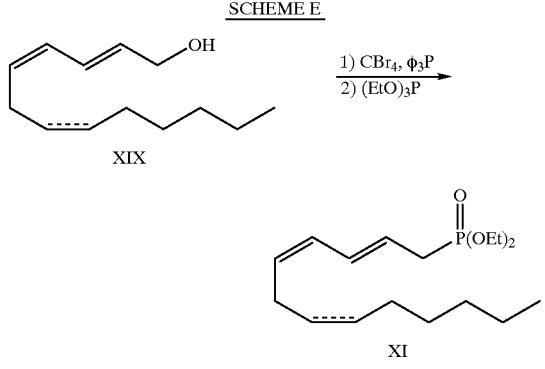

Scheme A shows two methods of making compounds of the present invention. In the first, an alkyl 3-(bromomethyl) benzoate is reacted with tetrahydrothiophene to form a sulfonium salt which is added to the appropriate aldehyde (V) under phase transfer conditions (OH⁻, benzyltriethylammonium chloride) to give the product (VI) which can optionally be saponified using an appropriate base to give the desired salt (VII).

Alternately, the compounds may be prepared by formation of the appropriate unsaturated sulfonium salt followed by addition of the sulfonium salt to alkyl 3-formylbenzoate under phase transfer conditions (OH⁻, Et₃BnNCl) to give the product (IX), optionally followed by saponification to the desired salt (VII).

Scheme B shows another method of preparing compounds of the invention in which alkyl 3-formylbenzoate is refluxed with (triphenylphosphoranylidene)acetaldehyde to form alkyl 3-(3-oxo-1E-propenyl)benzoate which is then oxidized to give the alkyl 3-(3-formyloxiranyl)benzoate (X). Coupling of (X) with the appropriate diethyl phosphonate (XI) in the presence of sodium hexamethyldisilazide(NaHMDS) gives the product (XII) which may optionally be saponified to give the desired salt.

In Scheme C alkyl 3-(bromomethyl)benzoate is reacted with tetrahydrothiophene to form a sulfonium salt which is then added to 1-(tert-butyldimethylsilyloxy)-4-butanone (XIII) to give alkyl 3-[3-(1-tert-butyldimethylsilyloxy-propyl)oxiranyl]benzoate (XIV). Reaction with tetrabutyl ammonium fluoride gives the alcohol which is oxidized with chromium (VI) oxide in the presence of pyridine to give alkyl 3-[3-(1-propanal) oxiranyl]benzoate (XV). Reaction of this compound with (triphenylphosphoranylidene) acetaldehyde gives alkyl 3-[3-(5-oxo-3E-pentenyl) oxiranyl]benzoate (XVI) which is reacted with 1-(triphenylphosphoranylidene)-3Z-nonene in the presence of hexamethylphosphoramide to give the product (XVII) which may optionally be saponified with an appropriate base to give the desired salt.

Schemes D and E illustrate the preparation of intermediates used to prepare the final products.

Scheme D shows a method of preparing an aldehyde which may be used in Scheme A. 1-Methoxy-1E-buten-3-yne is reacted with tributylstannane in the presence of catylytic 2,2'-azobisisobutyronitrile (AIBN) to give tributyl (4-methoxy-1E,3E-butadienyl)stannane which is then reacted with butyllithium followed by coupling with an appropriate aldehyde (XVIII). The alcohol-formed is reacted with toluene sulfonic acid (TSOH) to give the desired aldehyde (V).

Scheme E illustrates the preparation of the diethyl phosphonates. An appropriate alcohol (XIX) is reacted with carbon tetrabromide and triphenylphosphine followed by reaction with triethyl phosphite to give the diethyl phosphonate (XI).

Scheme F shows the preparation of a tert-butyldimethylsilyloxy alkanone. An appropriate diol such as 1,4-butanediol (XX) is reacted with tert-butyldimethyl-silyl chloride and the product is oxidized to the aldehyde (XIII) with pyridinium dichromate (PDC).

Compounds of the present invention are useful by reason of their valuable biological properties. They are inhibitors of $LTA_4$ hydrolase the enzyme which catalyzes the conversion of $LTA_4$ to $LTB_4$ which has been implicated as an important mediator of inflammation due to its potent proinflammatory properties.

Leukotrienes are a class of compounds released by various cell types including neutrophils (PMN) Gillard, J. et al., *Drugs of the Future*, 12:453–474 (1987). Leukotriene biosynthesis is initiated by a lipoxygenase reaction with arachidonic acid to produce 5S-HPETE, which in turn is dehydrated to form leukotriene-$A_4$ ($LTA_4$). $LTA_4$ is the substrate for a cytosolic enzyme, $LTA_4$ hydrolase which produces $LTB_4$, a compound with potent pro-inflammatory properties. $LTA_4$ hydrolase inhibition with subsequently reduced $LTB_4$ production may provide a mechanism for preventing or reducing inflammatory responses.

The activity of the compounds of the present invention was determined using the following tests.

A23187-Induced $LTB_4$ Production in Human Promyelocytic Leukemia HL-60 Cells.

Materials: Calcium ionophore A23187 was obtained from Calbiochem (La Jolla, Calif.). Trans-stilbene oxide was obtained from Sigma (St. Louis, Mis.). Hanks' balanced salt solution (HBSS) (10× concentrate), 1M Hepes, and Dulbecco's modified Eagle medium were obtained from GIBCO Laboratories (Grand Island, N.Y.). Fetal bovine serum was obtained from HyClone Laboratories (Logan, Utah). The $LTB_4$ and $PGE_2$ radioimmunoassay antibodies were purchased from Amersham International plc (Amersham, UK) and NEN Research Products (N. Billerica, Mass.), respectively. Reagents for assay of lactate dehydrogenase (LDH) activity were purchased from Beckman (Carlsbad, Calif.).

Preparation of HL-60 Cells: HL-60 cells were cultured in Dulbecco's modified Eagle medium (supplemented with 20% fetal bovine serum, 20 mM Hepes, 100 U/ml penicillin and 100 mcg/ml streptomycin) and maintained at 37° C. in a humidified atmosphere of 5% $CO_2$ in air. Cells from exponentially growing cultures were seeded at $3 \times 10^5$ cells/ml and induced to differentiate into granulocytes wth 0.8% (v/v) N,N-dimethylformamide for 4 days (1,2). Prior to assay, differentiated HL-60 cells were washed once with Hanks' balanced salt solution containing 0.35 mg/ml sodium bicarbonate and 10 mM Hepes, pH 7.3 (HBSS) and resuspended in HBSS at a concentration of $3 \times 10^6$ cells/ml. HL-60 cell viability was >95% as assessed by trypan blue exclusion.

HL-60 Cell Assay: DMSO or test compounds as 100× concentrates in DMSO were added in duplicate to 1.0 ml HL-60 cell suspensions ($3 \times 10^6$ cells) and preincubated at 37° C. for 10 minutes in a shaking water bath. After an additional 5 minute incubation with calcium ionophore A23187 (10 mcl @ $5 \times 10^{-4}$M in DMSO), the cells were pelleted at 12,800×g for 15 seconds and the supernatant removed and stored at −20° C. for quantification of $LTB_4$ or $PGE_2$ via radioimmunoassay and LDH activity.

Statistical Methods: $LTB_4$ and $PGE_2$ data were expressed as percent inhibition of A23187-stimulated controls. For $IC_{50}$ determinations, the 4 parameter logistic model was used where y is the percent inhibition response and x is the $\log_{10}$ concentration of the inhibitor:

$$y = \frac{y_x - y_0}{1 + [x/a]^b} + Y_0$$

Nonlinear regression was performed using the SAS (3) procedure NLIN to obtain least squares estimates of the four parameters in the above equation: $y_x$ (maximum), $Y_0$ (minimum), a ($\log_{10} IC_{50}$) and b (slope factor). Increases in mean LDH levels for A23187-stimulated cells in the presence of test compound were tested for significance using a one-tailed two sample Student's t-test.

References:

1. Fontana, J. A., D. A. Colbert, and A. B. Deisseroth. Identification of a Population of Bipotent Stem Cells in the HL60 Human Promyelocytic Leukemia Cell Line. *Proc. Nat. Acad. Sci. U.S.A.* 78:3863–3866, 1981.

2. Agins, A. P., A. B. Hollmann, K. C. Agarwal and M. C. wiemann. Detection of a Novel Cyclooxygenase Metabolite Produced by Human Promyelocytic Leukemia (HL-60) Cells. *Biochem. Biophys. Res. Comm.* 126:143–149, 1985.

3. SAS User's Guide: Statistics, Version 5 Edition, SAS Institute Inc., Cary, N.C., 1985.

Leukotriene —$A_4$ Hydrolase Inhibition Materials

Leukotriene-$A_4$-methyl ester and leukotriene-$A_3$ were purchased from Biomol (Cambridge). Trans-stilbene oxide, EDTA, phenylmethyl sulphonyl fluoride were purchased from Sigma (St. Louis). Eagles Basil Media was purchased from GIBCO (Grand Island). $LTB_4$ radioimmunoassay kit was purchased from Amersham (Arlington Heights, Ill.) (#Trk. 840).

Methods

Methods were modified from those reported by Evans et al., *Biochem. Biophys. Acta,* 840:43–50 (1985).

Rat Neutrophil Isolation

Male Sprague Dawley (CD1) rats (250–400 gm bodyweight) were given oyster glycogen, 1 mg/ml in 0.9% NaCl, by intraperitoneal injection. The animals were sacrificed after 8–20 hours and the peritoneal cavity washed with 10 ml Eagles Basil Medium (pH 7.4, 25 mM HEPES, without glutamine). The collected peritoneal lavage fluid was centrifuged at 150×G, 15 minutes at 4° C. to isolate the neutrophils. The supernatant was removed and the cell pellet was resuspended in 20 cc 10 mM sodium phosphate buffer, pH 7.0 with 2 mM Na-EDTA and 1 mM phenylmethyl sulphonyl fluoride (PMSF).

Leukotriene-$A_4$ Hydrolase Isolation

The cell suspensions, which were 90–95% neutrophils as determined by cytometry, were homogenized by a polytron at 4° C. with three 30 second bursts with cooling on ice in between. The homogenate was centrifuged at 100,000×G for 60 minutes, and the supernatant containing cytosolic $LTA_4$ hydrolase was obtained.

$LTA_4$ Methyl Ester Deesterificaiton $LTA_4$, the substrate for $LTA_4$ hydrolase, is supplied as the stable methyl ester that must be hydrolized to the active form. $LTA_4$-methyl ester (5000 ng) was dried under a stream of super-dry Argon (Matheson) to which was added a 1 ml methanol: 10M NaOH (9.8:0.2 v/v). The mixture was stirred 3 hours at 4° C. and used immediately.

$LTA_4$ Hydrolase Enzyme Assay

Supernatant containing $LTA_4$ hydrolase, 0.5 ml, was added to 0.5 ml Tris-acetate buffer, pH 7.8, containing 1 mg/ml fatty-acid free BSA. The mixture was incubated 3 minutes at 37° C. with 0.1 ml containing different enzyme inhibitor and test compound concentrations in DMSO. $LTA_4$, 25 ng in 20 μl methanol, was added and incubation with shaking continued at 37° C. for one minute. The reaction was quenched with 2 ml ice-cold ethanol. The quenched mixture was immediately frozen at –76° C. $LTB_4$ levels were determined by radioimmunoassay (RIA) with a validated commercial kit. Various concentrations of potential enzyme inhibitors were evaluated for inhibition of $LTB_4$ production using a standardized amount of enzyme and substrate. The amount of inhibitor necessary to reduce $LTB_4$ production by fifty percent was calculated as the $IC_{50}$ value for each inhibitor. $IC_{50}$ values were determined by least square linear regression analysis from the average ±SEM for 4 experiments.

Results for certain compounds of the present invention are given in Table 1.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

EXAMPLE 1

Methyl 3-[3-(1E-tetradecenyl)oxiranyl]benzoate

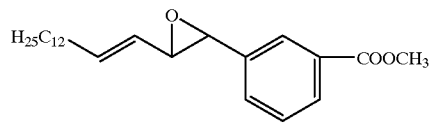

Methyl 3-(bromomethyl)benzoate (0.69 g, 3.0 mmol) was dissolved in 5 ml of 7% aqueous methanol. Tetrahydrothiophene (0.52 ml, 6.0 mmol) was added, and the mixture was stirred at room temperature (RT) for 1 hr. The solvents were removed and the residue was washed with hexane and dried. The crude sulfonium salt was suspended in 15 ml methylene chloride with benzyltriethylammonium chloride (0.075 g) and 2-pentadecenal (0.6 g, 2.67 mmol) at 0° C. Cooled 10 N sodium hydroxide (6 ml) was added. The mixture was stirred at 0° C. for 5 min. and at RT for 20 min. The product was flash chromatographed on silica gel using 100:1 hexane/ethyl acetate and 50:1 hexane/ethyl acetate as eluent. The product was recrystallized from hexane to give white crystals; melting point 43–44° C.

Analysis calculated for $C_{24}H_{36}O_3$.

Calc.: C, 77.38; H, 9.74.

Found: C, 77.31; H, 9.96.

The lithium salt of the title compound was prepared by stirring 10 mg of the ester prepared above in 1 mL methanol/ 0.2 mL tetrahydrofuran (THF) with 0.05 mL of 1N aq. LiOH at room temp for 24 hr. Concentration yielded the crude lithium salt.

TABLE 1

| Example No. | $LTA_4$ Hydrolase Enzyme Assay | | HL-60 Cell Assay | | | |
|---|---|---|---|---|---|---|
| | $IC_{50}$ (mM) | % Inhibition $10^{-4}$M | $IC_{50}$ (mM) | % Inhibition | | |
| | | | | $10^{-6}$M | $10^{-5}$M | $10^{-4}$M |
| 22 | — | 20 | — | — | I | 79 |
| 1,Li$^+$ salt | — | 40 | 2.8 | 26 | 96 | 94 |
| 4,Li$^+$ salt | 80 | 58 | 0.16 | 77 | 89 | 88 |
| 7,Li$^+$ salt | 2 | 85 | 15 | I | 61 | (80 at 5 × $10^{-5}$M) |
| 1 | — | — | — | — | — | I |
| 4 | — | — | — | — | I | 29 |

I = inactive at that concentration

EXAMPLE 2
3-[3-(1E-tetradecenyl)oxiranyl]benzoic acid

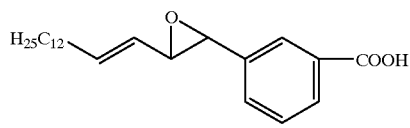

The ester prepared in Example I (0.075 g, 0.02 mmol) was stirred in 5 ml of methanol/0.55 ml tetrahydrofuran (THF). Aqueous lithium hydroxide (0.3 ml of 1N) was added and the mixture stirred at RT for 54 hrs. After 6 hr., another 0.2 ml of 1N lithium hydroxide was added. The reaction mixture was poured into ether/water (pH 6), and the ether layer was washed with water and saturated sodium chloride, dried over sodium sulfate and concentrated to give the product.

EXAMPLE 3
1-bromo-2E, 4E ,pentadecadiene

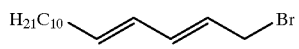

1,4E-pentadecadien-3-ol (0.45 g, 2.0 mmol) was stirred in 10 ml of ether at −40° C. and phosphorous tribromide (0.2 ml, 2.1 mmol) was added dropwise. The mixture was slowly warmed to 0° C. and stirred for 15 min. at 0° C.. The reaction mixture was poured into ice water, and the ether layer was washed with dilute sodium bicarbonate and saturated sodium chloride then dried over magnesium sulfate and concentrated. The crude product was chromatographed by flash chromatography on a column deactivated with methyl alcohol then acetone then ethyl acetate then hexane with 5% triethylamine to give the pure product.

EXAMPLE 4
Methyl 3-[3-(1E,3E-tetradecadienyl)oxiranyl]benzoate

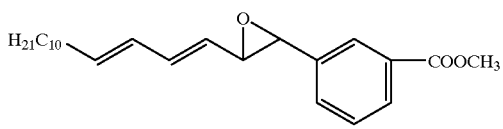

The product of Example 3 (0.40 g, 1.39 mmol) which was approximately 70% pure was stirred in 4.0 ml of 7% aqueous methanol with 0.25 ml (2.8 mmol) of tetrahydrothiophene at RT for 1 hr. The solvents were removed, and the residue was washed with pentane and dried. The crude salt was dissolved in 5.0 ml of methylene chloride along with 0.02 g of benzyltriethylammonium chloride and 0.80 g (0.487 mmol) of methyl 3-formylbenzoate, and the mixture was cooled to −15° C. To this reaction mixture 2.0 ml of cooled 8N potassium hydroxide was added, and the mixture was stirred at 0° C. for 15 min. The pure product (35 mg) was precipitated from pentane, m.p. 53–54.5° C.
Analysis calculated for $C_{24}H_{34}O_3$.
Calc.: C, 77.80; H, 9.25.
Found: C, 77.16; H, 9.28.
The lithium salt of the title compound was prepared by the same procedure used in Example 1.

EXAMPLE 5
Tributyl(4-methoxy-1E,3E-butadienyl)stannane

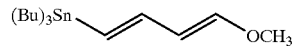

1-Methoxy-1E-buten-3-yne (100 ml) was purified as described in *J. Org. Chem.* 1983, p. 2114. to provide approximately 25 g of colorless liquid boiling at 58–61° C./at approximately 85 mm pressure. The purified alkyne (5.4 g, 65.8 mmol) and tributylstannane (17.7 ml, 65.8 mmol) were heated at about 90° C. with catalytic 2,2'-azobisisobutyronitrile for 14 hrs. The mixture was distilled at 145–150° C./0.6 mm pressure to provide 19.8 g (0.053 mol), 80%, of a light yellow liquid. (literature b.p. 120–130° C./0.3 mm pressure) NMR analysis indicated the presence of at least 3 geometric isomers.

EXAMPLE 6
2E,4E,6E-pentadecatrienal

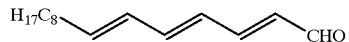

To 3.0 g (8.04 mmol) of the product of Example 5 in 30 ml tetrahydrofuran (THF) at −78° C. was added dropwise 5.1 ml of 1.6M butyl lithium (8.16 mmol). The reaction mixture was stirred at −78° C. for 1 hr. and then 1.25 g (7.43 mmol) of 2E-undecenal in 5 ml THF was added, and the mixture was stirred at −78° C. for 3 hrs. The reaction was quenched with aqueous sodium bicarbonate and the organic layer washed with saturated sodium chloride, dried over sodium sulfate, and concentrated. The crude alcohol was stirred in 35 ml of 5% aqueous THF with 5 mol % 4-methylbenzene-sulfonic acid ● $H_2O$ for 1 hr. at RT. The mixture was poured into water and the organic layer was washed with water and saturated sodium chloride, dried over sodium sulfate and concentrated to a yellow oil. Flash chromatography with hexane, followed by 20:1 hexane/ethyl acetate gave the product as a light yellow oil, all trans.

EXAMPLE 7
Methyl 3-[3-(1E,3E,5E-tetradecatrienyl)oxiranyl]benzoate

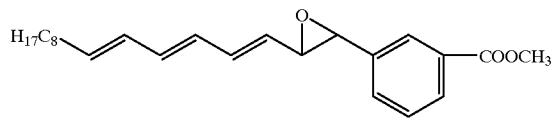

Methyl 3-(bromomethyl)benzoate (0.46 g, 2.0 mmol) was stirred in 5 ml 7% aqueous methanol with 0.35 ml (4.0 mmol) tetrahydrothiophene at RT for 1 hr. The solvents were removed, and the residue was washed with pentane and dried. The crude salt was stirred in 10 ml of methylene chloride with 0.05 g of benzyltriethylammonium chloride and 0.40 g (1.81 mmol) of the product of Example 6 and cooled to −15° C. Cooled 8N potassium hydroxide (4.0 ml) was added, and the mixture was stirred at 0° C. for 15 min. The mixture was poured into ether/water and the ether layer was washed 3× with water and 1× with saturated sodium chloride then dried over sodium sulfate and concentrated to yield a light yellow solid as the product. The crude product was crystallized from pentane/ether to provide the pure product as white crystals, m.p. 75–76.5° C.
Analysis calculated for $C_{24}H_{32}O_3$.

Calc.: C, 78.22; H, 8.75.
Found: C, 77.93; H, 8.88.

The lithium salt of the title compound was prepared using the procedure described in Example 1.

EXAMPLE 8
Methyl 3-(3-oxo-1E-propenyl)benzoate

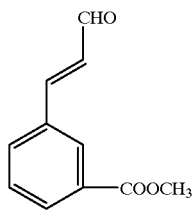

Methyl 3-formylbenzoate (0.65 g, 3.96 mmol) and (triphenylphosphoranylidene) acetaldehyde (1.33 g, 4.36 mmol) were refluxed in 30 ml of benzene for 17 hrs. The reaction mixture was cooled and concentrated. Flash chromatography on silica gel using 15:1 then 6:1 hexane/ethyl acetate as eluent gave the transenal product as a white solid, m.p. 71–75° C.
Analysis calculated for $C_{11}H_{10}O_3$.
Calc.: C, 69.46; H, 5.30.
Found: C, 69.22; H, 5.29.

EXAMPLE 9
Methyl 3-formylbenzoate

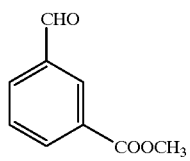

Methyl 3-formylbenzoic acid (3.0 g, 20 mmol) was stirred in 100 ml of ether at 0° C. An ethereal diazomethane solution was added until the yellow color persisted. The solution was then concentrated. The crude product was precipitated from ether/pentane to yield 2.98 g (18.15 mmol) of the product as a white solid.

EXAMPLE 10
Methyl 3-(3-formyloxiranyl)benzoate

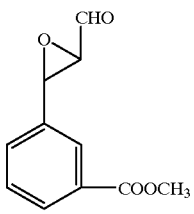

(a) Methyl 3-(3-oxo-1E-propenyl)benzoate (0.57 g, 3.0 mmol) and 4.43M 1,1-dimethylethylhydroperoxide (0.9 ml, 4.0 mmol) in isooctane were stirred in 3.0 ml of dimethylsulfoxide (DMSO) at RT. 1N tetrabutylammonium fluoride in THF was added in 6 portions at 10 minute intervals, and the mixture was stirred for 45 min. after the last portion was added. The reaction mixture was diluted with water and extracted with ethyl acetate. The ethyl acetate extract was washed with water and brine, dried over sodium sulfate, and concentrated. Flash chromatography using 10:1 followed by 3:1 hexane/ethyl acetate provided 0.030 g of the trans epoxide and 0.42 g of trans/cis epoxides (7:1 mixture).

(b) Methyl 3-(3-oxo-1E-propenyl)benzoate (0.67 g, 3.52 mmol) and 10 ml of methanol was added dropwise to 0.58 ml of 70% 1,1-dimethylethylhydroperoxide (4.2 mmol) in 5 ml of methanol. The pH was maintained at pH 8.0–8.5 throughout with 1N sodium hydroxide. The mixture was stirred at about 35° C. for 1.5 hrs. The reaction mixture was poured into ether/water and the ether layer was washed 3× with water and 1× with brine, dried over sodium sulfate, and concentrated. Flash chromatography using 10:1 followed by 2:1 hexane/ethyl acetate provided the product, methyl trans-3-(3-formyloxiranyl)benzoate as the pure trans epoxide.
Analysis calculated for $C_{11}H_{10}O_4$.
Calc.: C, 63.52; H, 4.94.
Found: C, 63.56; H, 4.97.

EXAMPLE 11
Diethyl 2E,4Z-tridecadienylphosphonate

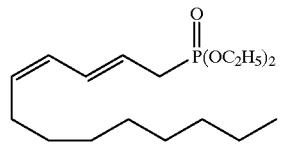

To 0.78 g (4.0 mmol) of 2E,4Z-tridecadien-1-ol, 1.6 g (4.8 mmol) carbon tetrabromide, and 0.40 g (4.8 mmol) sodium bicarbonate in 20 ml of methylene chloride at 0° C. was added 1.36 g (5.2 mmol) of triphenylphosphine in portions, and the mixture was stirred at 0° C. for 1 hr. Triethylphosphite (1.16 ml, 6.8 mmol) was added and the mixture was stirred in the dark at RT for five days. The reaction mixture was concentrated, dissolved in ether, and filtered to remove the triphenylphosphine oxide byproduct. Flash chromatography on silica gel using 5:1 followed by 3:1 hexane/ethyl acetate as eluent gave the product.

EXAMPLE 12
Methyl 3-[3-(1E,3E,5Z-tetradecatrienyl)oxiranyl]benzoate

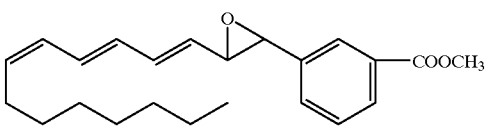

To 0.05 g (0.158 mmol) of the product prepared in Example 11 in 2 ml THF at −18° C. was added 0.17 mL (0.17 mmol) of 1M sodium hexamethyldisilazide in THF. The mixture was stirred at −78° C. for 5 min and 0.033 g (0.158 mmol) of the product prepared in Example 10 in 1 mL THF was added. The reaction mixture was stirred at −78° C. for 1.5 hr., at 0° C. for 1.0 hr., and at RT for 20 hr. The mixture was diluted with ether and quenched with water. The ether layer was washed with brine, dried over sodium sulfate, and concentrated to give a yellow oil. The product was flash chromatographed on a deactivated silica gel column and eluted with 25:1:1 hexane/ethyl acetate/triethylamine to provide a mixture of methyl 3-[3-(1E,3E,5Z-tetradecatrienyl)oxiranyl]benzoate and methyl 3-(1E,3E,5Z-tetradecatrienyl)benzoate and a relatively pure methyl 3-[3-(1E,3E,5Z-tetradecatrienyl)oxiranyl]benzoate. The mixture was separated by chromatography on silica gel deactivated with ethyl acetate using hexane (2.5% triethylamine) followed by 50:1:1 hexane/ethyl acetate/triethylamine to give the product.

The lithium salt of the title compound was prepared by the procedure used in Example 1.

EXAMPLE 13
Diethyl 2E,4Z,7Z-tridecatrienylphosphonate

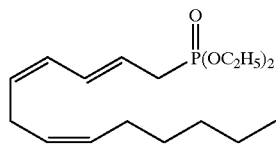

2E,4Z,7Z-tridecatrien-1-ol (0.39g, 2.0 mmol), carbon tetrabromide (0.80 g, 2.4 mmol), and sodium bicarbonate (0.20 g, 2.4 mmol) were stirred in 10 ml of methylene chloride at 0° C. Triphenylphosphine (0.6 g, 2.6 mmol) was added in portions, and after one hour at 0° C., triethylphosphite (0.58 g, 3.4 mmol) was added. The reaction mixture was stirred at RT for 3-½ days. The reaction mixture was concentrated and flash chromatographed using 5:1 followed by 3:1 hexane/ethyl acetate to provide the product.

EXAMPLE 14
Methyl 3-[3-(1E,3E,5Z,8Z-tetradecatetraenyl)oxiranyl]benzoate

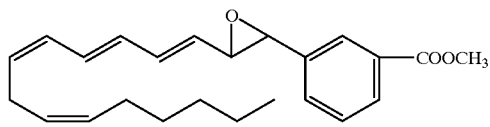

To diethyl 2E,4Z,7Z,tridecatrienylphosphonate (0.05 g, 0.159 mmol) in 2.0 ml THF at −78° C. was added 0.17 ml of 1M sodium hexamethyldisilazide in THF, and the bright yellow solution was stirred at −78° C. for 5 min. Methyl 3-(3-formyloxiranyl)benzoate (0.033 g, 0.158 mmol) and 1.0 ml THF was added, and the mixture was stirred at −78° C. for 1 hr., at 0° C. for 1 hr., and at RT for 21 hr. The mixture was diluted with ether and quenched with water. The ether layer was washed with brine, dried over sodium sulfate, and concentrated. Flash chromatography on a silica gel column deactivated with ethyl acetate and using hexane (2% triethylamine) followed by 50:1:1 hexane/ethyl acetate/triethylamine gave the product.

EXAMPLE 15
1-(tert-Butyldimethylsilyloxy)-4-butanol

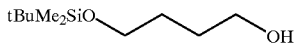

tBuMe$_2$SiO=tert-butyldimethylsilyloxy
1,4-Butanediol (9.0 g, 100 mmol), tert-butyldimethylsilyl chloride (15.1 g, 100 mmol), and imidazole (13.6 g, 200 mmol) were stirred in 100 ml of dimethylformamide (DMF) at room temperature for 21 hrs. The reaction mixture was poured into ether/water and the ether layer was washed twice with water and once with saturated sodium chloride, dried over sodium sulfate, and concentrated. Flash chromatography on silica gel with 20:1 then 2:1 hexane/ethyl acetate as eluent gave the product.

EXAMPLE 16
1-(tert-butyldimethylsilyloxy)-4-butanone

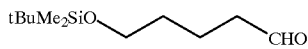

The product of Example 15 (8.0 g, 39 mmol) was stirred in 150 ml of methylene chloride with pyridinium dichromate (22 g, 58 mmol) and about 3 g of Celite® filter agent at RT for 6 hrs. The mixture was filtered through silica and concentrated by rotary evaporation. Flash chromatography on silica gel using 100:1 then 20:1 hexane/ethyl acetate gave the product.

EXAMPLE 17
Methyl trans-3-[3-(1-tert-butyldimethylsilyloxypropyl)-oxiranyl]benzoate

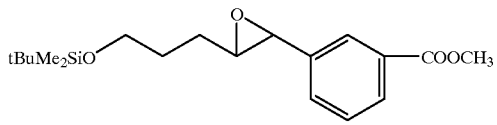

Methyl 3-(bromomethyl)benzoate (0.92 g, 4.0 mmol) was stirred in 7.0 ml of 7% aqueous methanol. Tetrahydrothiophene (0.71 ml, 8.0 mmol) was added, and the reaction mixture was stirred at RT for 1 hr. The solvents were removed, and the residue was washed with pentane and dried. The crude salt was stirred in 15.0 ml of methylene chloride with 0.10 g of benzyltriethylammonium chloride and the product of Example 16 (0.70 g, 3.46 mmol) and the mixture was cooled to 0° C. Cooled 8N potassium hydroxide (10.0 ml) was added, and the reaction mixture was warmed to RT and stirred for 30 min. The reaction mixture was poured into ether/water, and the ether layer was washed with water and saturated sodium chloride, dried over sodium sulfate and concentrated. Flash chromatography on silica gel with 50:1 then 35:1 hexane/ethyl acetate as eluent gave the product as the trans isomer (0.54 g), the cis isomer (0.02 g) and a mixture of the two (0.56 g).
Analysis (mixture) calculated for $C_{19}H_{30}SiO_4$.
Calc.: C, 65.10; H, 8.63.
Found: C, 65.10; H, 8.90.

EXAMPLE 18
Methyl trans-3-[3-(1-hydroxypropyl)oxiranyl]benzoate

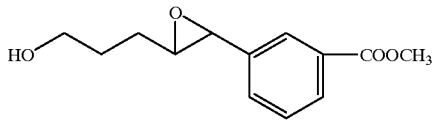

The product of Example 17 (0.60 g, 1.71 mmol) was stirred in 25 ml of THF with 5 drops of acetic acid. To this was added 3.4 ml of 1N tetrabutylammonium fluoride in THF and the reaction mixture was stirred at RT for 18 hr. then poured into ether/water. The ether layer was washed with water and saturated sodium chloride, dried over sodium sulfate, and concentrated. Flash chromatography on silica gel using 5:1 then 1:1 hexane/ethyl acetate as eluent gave the product as a colorless gum.
Analysis: Calculated for $C_{13}H_{16}O_4$.
Calc.: C, 66.09; H, 6.83.
Found: C, 65.77; H, 6.98.

EXAMPLE 19
Methyl trans-3-[3-(1-propanal)oxiranyl]benzoate

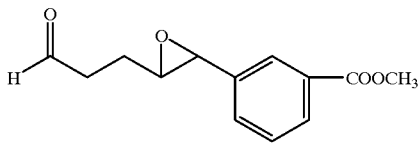

Chromium (VI) oxide (0.20 g, 2.0 mmol) was added to pyridine (0.32 ml, 3.8 mmol) in 15 ml of methylene chloride, and the reaction mixture was stirred at RT for 15 min. Celite® filter agent (0.5 g) and the product from Example 18 in 5.0 ml of methylene chloride were added, and the mixture was stirred at RT for 1.5 hrs. then filtered through silica gel and concentrated. Flash chromatography on silica gel with 5:1 then 2:1 hexane/ethyl acetate provided the product.
Analysis: Calculated for $C_{13}H_{14}O_4$.
Calc.: C, 66.66; H, 6.02.
Found: C, 66.34; H, 6.11.

EXAMPLE 20
Methyl trans-3-[3-(5-oxo-3E-pentenyl)oxiranyl]benzoate

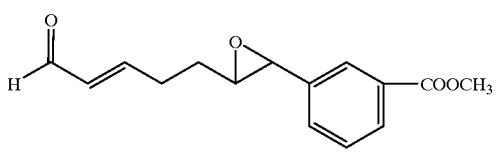

The product of Example 19 (0.13 g, 0.55 mmol) was refluxed in 5.0 ml of benzene with (triphenylphosphoranylidene) acetaldehyde (0.184 g, 0.605 mmol) for 23 hrs. The reaction mixture was cooled, diluted with hexane, filtered, and concentrated. Flash chromatography on silica gel with 10:1 then 2:1 hexane/ethyl acetate provided the product.
Analysis calculated for $C_{15}H_{16}O_4$.
Calc.: C, 69.22; H, 6.20.
Found: C, 69.20, H, 6.50.

EXAMPLE 21
Methyl 3-[3-(3-(E,5Z,8E-tetradecatrienyl)-oxiranyl]benzoate

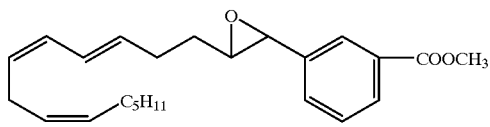

1-(triphenylphosphoranylidene)-3Z-nonene (0.139 g, 0.36 mmol) was stirred in 10.0 ml of THF and cooled to −78° C. One equivalent of butyllithium was added, and the orange solution was stirred at −78° C. for 20 min. Hexamethylphosphoramide(0.68 ml, 3.9 mmol) was added followed by the product of Example 20 (0.085 g, 0.327 mmol) in 3.0 ml of THF. The reaction mixture was stirred at −78° C. for 15 min. then quenched with saturated ammonium chloride. The organic layer was washed three times with water and once with brine, dried over sodium sulfate, and concentrated to provide the crude product. Flash chromatography of the crude product on silica gel using 100:1 then 20:1 hexane/ethyl acetate as eluent gave the product.
Analysis calculated for $C_{24}H_{32}O_3$.

Calc.: C, 78.22; H, 8.75.
Found: C, 78.25; H, 8.97.
The lithium salt was prepared by the procedure used in Example 1.

EXAMPLE 22
Methyl 3-(3-tetradecyloxiranyl)benzoate

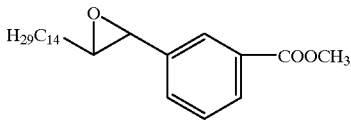

Methyl 3-(bromomethyl)benzoate (0.92 g, 4.0 mmol) was dissolved in 5.0 ml of 7% aqueous methanol. Tetrahydrothiophene (0.70 ml, 8.0 mmol) was added, and the mixture was stirred at room temperature for 1 hr. The solvent was removed, the residue was washed with hexane, and the crude salt was dried under vacuum. The crude salt was suspended in 25 ml of methylene chloride with benzyltriethylammonium chloride (0.10 g) and 1-pentadecanal (0.85 g, 3.75 mmol) at 0° C. To the suspension was added 8.0 ml of 10 N sodium hydroxide at 0° C. The reaction mixture was stirred at 0° C. for 5 min. and at room temperature for 20 min. then poured into ether/water. The ether layer was washed with water and saturated sodium chloride, dried over sodium sulfate, and concentrated. The crude white solid was flash chromatographed on silica gel using 100:1 then 50:1 hexane/ethyl acetate as eluent to give 0.73 g of product which was mostly trans and 0.33 g of a mixture.
The trans product (0.73 g) was dissolved in 5 ml of warm hexane. Cooling at 0° C. gave the product as a precipitate of white powder, m.p. 44–45° C.
The lithium salt of the product was prepared as described in Example 1.

What is claimed is:
1. A pharmaceutical composition for the treatment of inflammatory diseases comprising a therapeutically effective amount of a compound of the formula

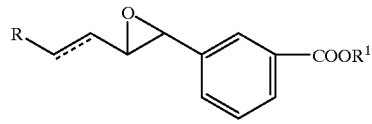

or a pharmaceutically acceptable salt thereof, wherein R is alkyl of 12 to 16 carbon atoms, alkenyl of 12 to 16 carbon atoms having from 1 to 4 —CH=CH— groups, aryl, heterocyclo, alkoxyalkyl wherein the alkyl groups have 1 to 6 carbon atoms, or aryloxyalkyl wherein the alkyl group has 1 to 6 carbon atoms; R' is hydrogen or lower alkyl; and a pharmaceutically acceptable carrier.
2. A pharmaceutical composition for the treatment of inflammatory disease comprising a therapeutically effective amount of the compound of the formula

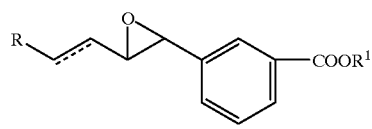

or a pharmaceutically acceptable salt thereof wherein R is alkyl of 12 carbon atoms, alkenyl of 12 carbon atoms having from 1 to 4 —CH═CH— groups when the carbon adjacent to R is saturated and from 1 to 2 —CH═CH— groups when the carbon adjacent to R is unsaturated, aryl, heterocyclo, alkoxyalkyl wherein the alkyl groups have 1 to 6 carbon atoms, or aryloxyalkyl wherein the alkyl group has 1 to 6 carbon atoms; and $R^1$ is hydrogen, lower alkyl, or a pharmaceutically acceptable cation; and a pharmaceutically acceptable carrier.

3. A pharmaceutical composition according to claim 2 for the treatment of inflammatory disease wherein R is alkyl of 12 carbon atoms, alkenyl of 12 carbon atoms having from 1 to 3 —CH═CH— groups when the carbon adjacent to R is saturated and from 1 to 2 —CH═CH— groups when the carbon adjacent to R is unsaturated, aryl, heterocyclo, alkoxyalkyl wherein the alkyl groups have 1 to 6 carbon atoms, or aryloxyalkyl wherein the alkyl group has 1 to 6 carbon atoms; and $R^1$ is hydrogen lower alkyl, or a pharmaceutically acceptable cation.

4. A pharmaceutical composition according to claim 3 for the treatment of inflammatory disease wherein R is alkyl of 12 carbon atoms; or alkenyl of 12 carbon atoms having from 1 to 3 —CH═CH— groups when the carbon adjacent to P is saturated and from 1 to 2 —CH═CH— groups when the carbon adjacent to R is unsaturated: $R^1$ is hydrogen or alkyl of from 1 to 4 carbon atoms; or a pharmaceutically acceptable salt thereof.

5. A pharmaceutical composition according to claim 3 for the treatment of inflammatory disease wherein R is alkyl of 12 carbon atoms or alkenyl of 12 carbon atoms having from 1 to 2 —CH═CH— groups: R is hydrogen or alkyl of from 1 to 4 carbon atoms; or a pharmaceutically acceptable salt thereof.

6. A pharmaceutical composition to claim 3 for the treatment of inflammatory disease wherein R is alkenyl of 12 carbon atoms having from 1 to 2 —CH═CH— groups, $R^1$ is hydrogen or alkyl of from 1 to 4 carbon atoms; or a pharmaceutically acceptable salt thereof.

7. A pharmaceutical composition according to claim 3 for the treatment of inflammatory disease wherein the compound is 3-[3-(1E-tetradecenyl)oxiranyl]benzoic acid, lithium salt.

8. A pharmaceutical composition according to claim 3 for the treatment of inflammatory disease wherein the compound is methyl 3-[3-(1E,3E-tetradecadienyl)-oxiranyl]benzoate.

9. A pharmaceutical composition according to claim 3 for the treatment of inflammatory disease wherein the compound is 3-[3-(1E,3E-tetradecadienyl)oxiranyl]benzoic acid, lithium salt.

10. A pharmaceutical composition according to claim 3 for the treatment of inflammatory disease wherein the compound is methyl 3(3-tetradecyloxiranyl)benzoate.

11. A pharmaceutical composition according to claim 3 for the treatment of inflammatory disease wherein the compound is 3-(3-tetradecyloxiranyl) benzoate, lithium salt.

* * * * *

UNITED STATES PATENT AND TRADEMARK OFFICE
CERTIFICATE OF CORRECTION

PATENT NO. : 5,990,326  Page 1 of 2
DATED : November 23, 1999
INVENTOR(S) : Stevan Wakefield Djuric et al.

It is certified that error appears in the above-identified patent and that said Letters Patent is hereby corrected as shown below:

Column 8,
Scheme F, " 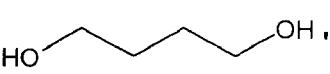 " should read -- 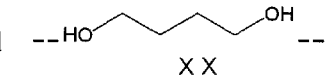 -- and

" 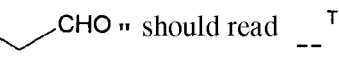 " should read -- 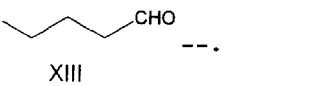 --.

Column 9,
Line 13, "tert" should read -- tert --;
Line 62, "The activity" should read -- ¶ The activity --; and
Line 64, "A23187-Induced" should read -- ¶ A23187-Induced --.

Column 10,
Line 10, "Preparation of" should read -- ¶ Preparation of --;
Line 24, "HL-60 Cell" should read -- ¶ HL-60 Cell --;
Line 32, "Statistical Methods:" should read -- ¶ Statistical Methods --;
Line 55, "wiemann" should read -- Wiemann --; and
Line 60, "Leukotriene-$A_4$" should read -- ¶ Leukotriene-$A_4$ --.

Column 11,
Line 4, "Rat Neutrophil" should read -- ¶ Rat Neutrophil --;
Line 16, "Leukotriene-$A_4$" should read -- ¶ Leukotriene-$A_4$ --;
Line 23, "$LTA_4$ Methyl" should read -- ¶ $LTA_4$ Methyl --; and
Line 30, "$LTA_4$ Hydrolase" should read -- ¶ $LTA_4$ Hydrolase --.

Column 13,
Line 21, "1-bromo-2E, 4E ,pentadecadiene" should read
-- 1-bromo-2E,4E,pentadecadiene --.

Column 15,
Line 23, "transenal" should read -- trans enal --; and
Line 60, "$1,_1$-dimethylethylhydroperoxide" should read
--1,1-dimethylethylhydroperoxide--.

Column 18,
Line 2, "tert" should read -- tert --; and
Line 17, "tert" should read -- tert --.

UNITED STATES PATENT AND TRADEMARK OFFICE
CERTIFICATE OF CORRECTION

PATENT NO.    : 5,990,326
DATED         : November 23, 1999
INVENTOR(S)   : Stevan Wakefield Djuric et al.

It is certified that error appears in the above-identified patent and that said Letters Patent is hereby corrected as shown below:

Column 19,
Line 44, "3-[3-(3-(E,5Z,8E-tetradecatrienyl)" should read
-- 3-[3-(3-E,5Z,8E-tetradecatrienyl) --.

Column 20,
Line 66, "thereof" should read -- thereof, --.

Column 21,
Line 17, "hydrogen" should read -- hydrogen, --; and
Line 22, "P" should read -- R --.

Column 22,
Line 1, "R" should read -- $R^1$ --;
Line 4, "Composition" should read -- composition according --; and
Line 23, "3(3-tetradecyloxiranyl)benzoate" should read -- 3-(3-tetradecyloxiranyl) benzoate --.

Signed and Sealed this

Twenty-eighth Day of January, 2003

JAMES E. ROGAN
*Director of the United States Patent and Trademark Office*